US00PP29933P3

(12) United States Plant Patent
Maillard et al.

(10) Patent No.: US PP29,933 P3
(45) Date of Patent: Dec. 4, 2018

(54) NECTARINE TREE NAMED 'CAKESTAR'

(50) Latin Name: ***Prunus persica* (L.) Batsch**
Varietal Denomination: CAKESTAR

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 15/732,467

(22) Filed: Nov. 17, 2017

(65) Prior Publication Data

US 2018/0153067 P1 May 31, 2018

(30) Foreign Application Priority Data

Nov. 25, 2016 (QZ) ..... PBR 2016/2953

(51) Int. Cl.
*A01H 5/08* (2018.01)
*A01H 6/74* (2018.01)

(52) U.S. Cl.
USPC ..... Plt./188
CPC ..... *A01H 6/7454* (2018.05); *A01H 5/08* (2013.01)

(58) Field of Classification Search
USPC ..... Plt./188
CPC ..... A01H 5/0856
See application file for complete search history.

*Primary Examiner* — Kent L Bell
(74) *Attorney, Agent, or Firm* — Westerman, Hattori, Daniels & Adrian, LLP

(57) ABSTRACT

A new and distinct variety of white flat nectarine tree denominated 'CAKESTAR' has fruits with high eating quality and very long shelf life without alteration before and after harvesting, with a very well closed pistillary basin, with a semi-sweet white flesh, with a slightly red pigmentation under the fruit skin at ripening time and into the stone cavity, and an attractive luminous skin colored with a purple red blush on the whole skin surface.

4 Drawing Sheets

Botanical classification: *Prunus persica* (L.) Batsch.
Variety denomination: 'CAKESTAR'.

This application claims priority of Community plant variety right No. 2016/2953 filed on Nov. 25, 2016 which is hereby incorporated by reference in its entirety.

BACKGROUND OF THE NEW VARIETY

The present invention relates to a new and distinct variety of white flat nectarine tree, *Prunus persica* (L.) Batsch, which has been given the variety denomination 'CAKESTAR'.

This new tree produces fruits with a long shelf life without alteration both on the tree after growth completion and after harvesting, very good eating quality, semi-clingstone white flesh fruits with a slightly red pigmentation near the epidermis and into the stone cavity, for fresh market in July in the Pyrénées-Orientales department, France.

ORIGIN OF THE VARIETY

The 'CAKESTAR' white flat nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'CAKESTAR' variety results from controlled cross between the 'CAKEDELICE' white flat nectarine tree (not patented) which was used as the seed parent and the 'NECTARPERF' white nectarine tree (U.S. Plant Pat. No. 23,357) which was used as the pollen parent.

The 'CAKESTAR' variety was obtained by hybridizing and propagated by grafting on a 'INRA® GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'CAKESTAR' white flat nectarine tree blooms at the end of February or early in March near Elne in the Pyrénées-Orientales department, France. The blooming period is considered medium. However, it was observed that its late date of blooming seems to be highly dependant on climatic conditions.

The first fruit of 'CAKESTAR' ripens generally at medium season, in the beginning or middle of July. More particularly, it usually ripens between July 4$^{th}$ and July 18$^{th}$. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
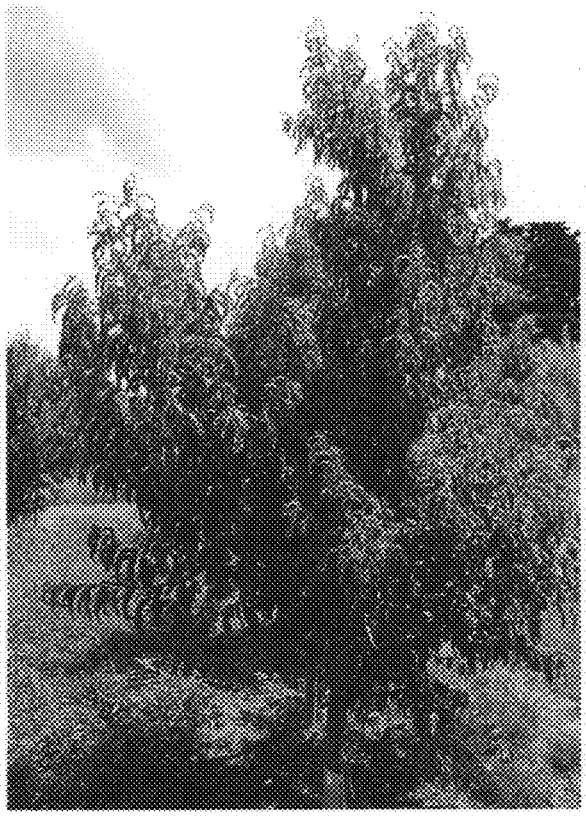
FIG. 1 is a color photograph which shows a view of a tree of the new variety in orchard, bearing fruits.
Figure 2:
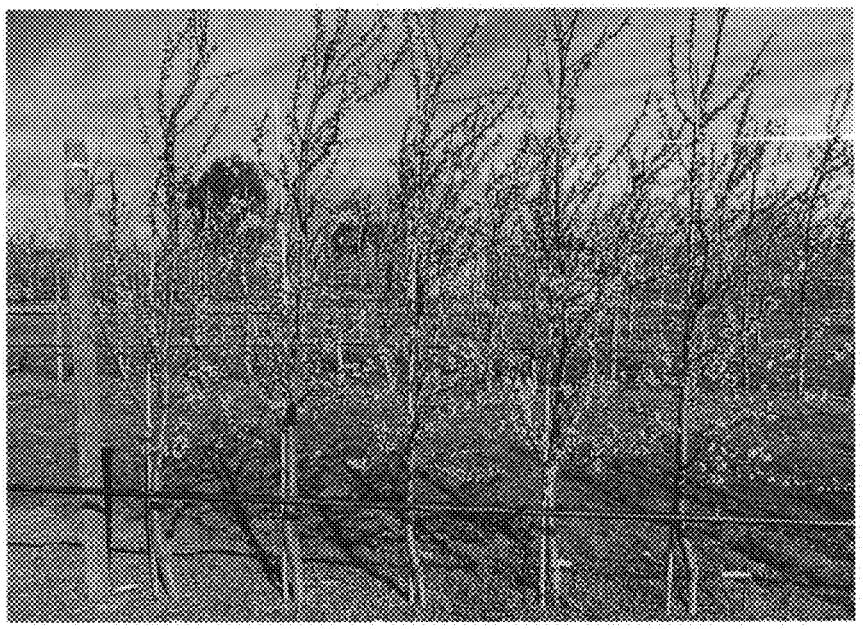
FIG. 2 is a color photograph which shows a view of five trees of the new variety in orchard at flowering time.
Figure 3:
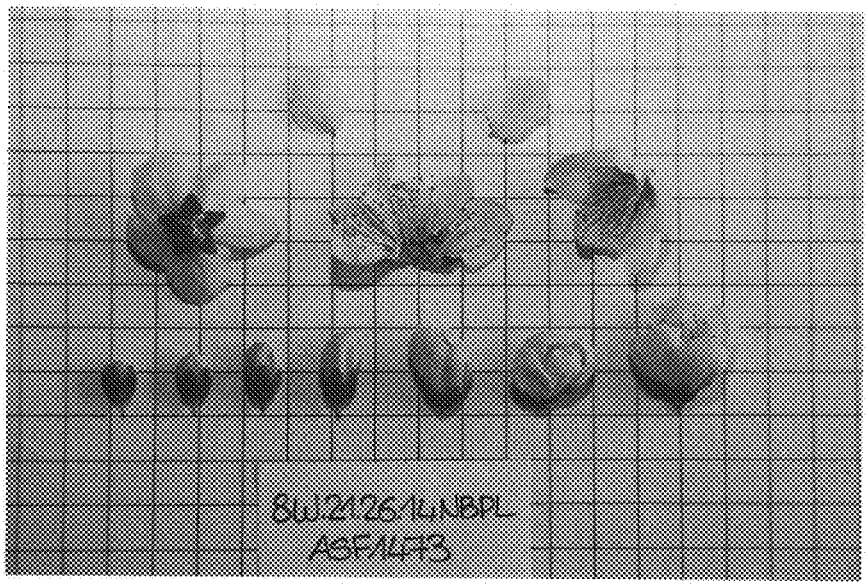
FIG. 3 is a color photograph which depicts the flower buds at different development stages, and the reverse and side view of the flower and the reproductive organs with petals removed, of the new variety.
Figure 4:
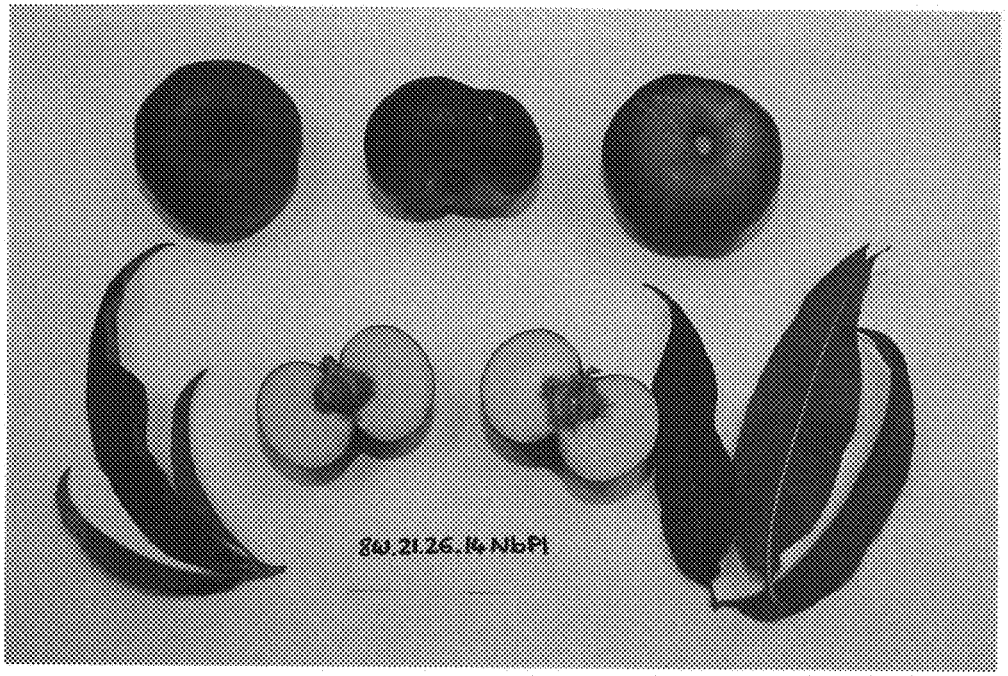
FIG. 4 is a color photograph that shows a close view of four typical specimens of the fruit of the new variety 'CAKESTAR' at ripening time, one fruit having been cut in half with the pit being left in one of the halves for depicting leaves, fruit flesh, pit and pit cavity of the new variety.
Figure 5:
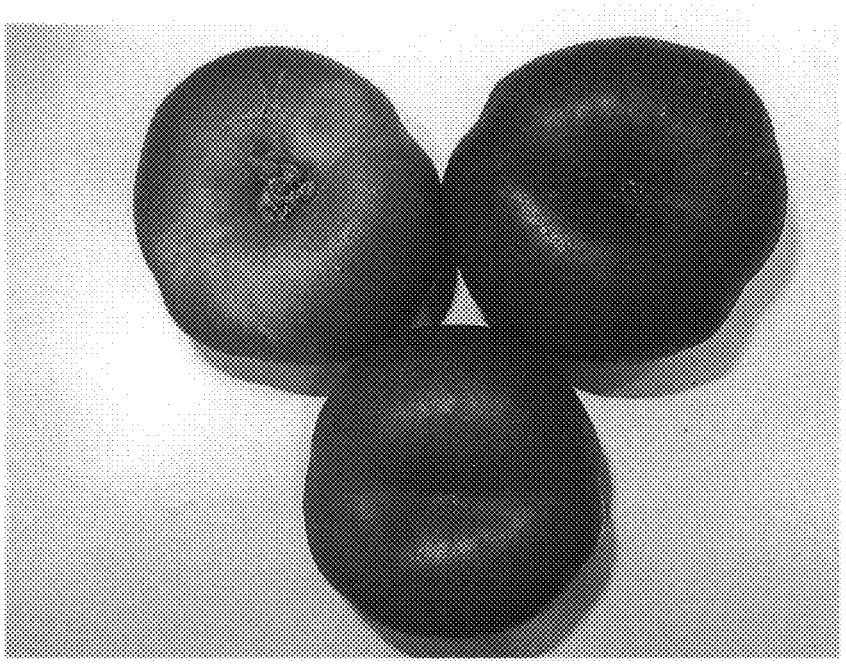
FIG. 5 is a color photograph that shows a close view of three typical specimens of the fruit of the new variety 'CAKESTAR' at ripening time.
Figure 6:
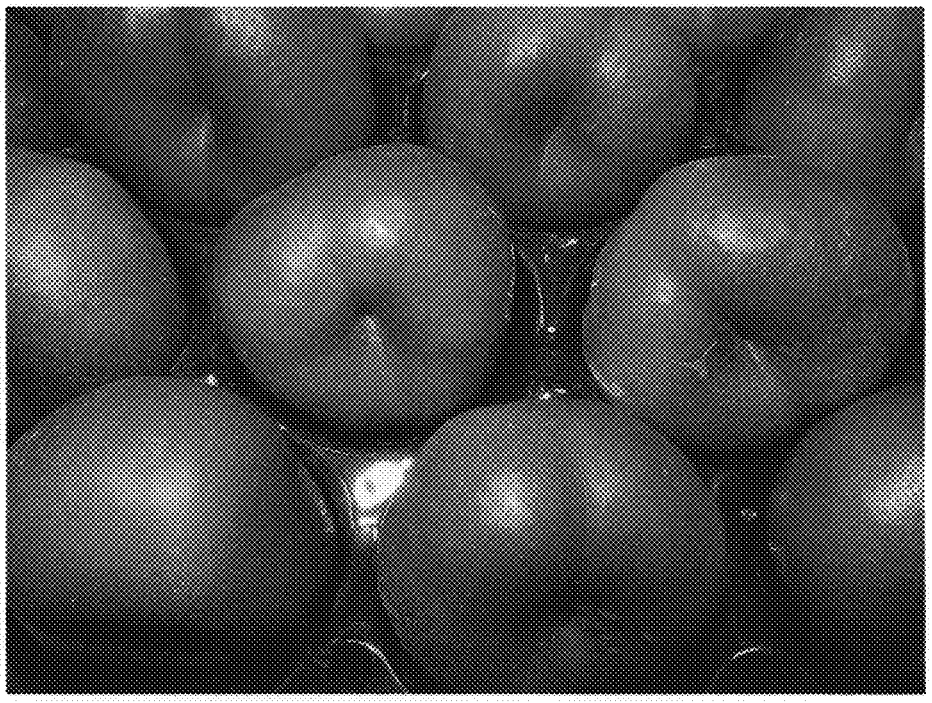
FIG. 6 is a color photograph that shows a close view of typical specimens of the fruit of the new variety 'CAKESTAR' at ripening time.
Figure 7:
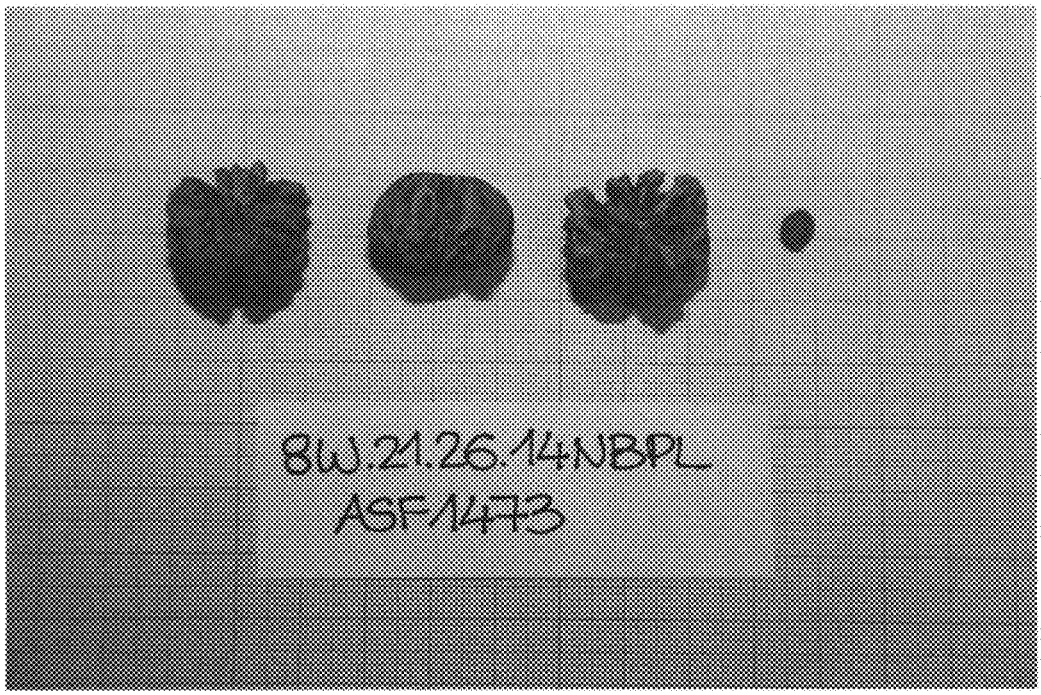
FIG. 7 is a color photograph of the stone of the new variety and the kernel of the stone.

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'CAKESTAR' is high, due to fruit very long shelf life without alteration after harvesting.

Trees are vigorous and large stature half-standing in a semi-flared out aspect. The anthocyanic coloration of flowering shoot is present excluding brushwood side away from sun. The time of beginning of flowering is considered medium; flowering begins at the end of February or during March. The type of flower is showy (rosette) with medium to large petal size. Petals are medium pink or pink. Leaf glands are present and reniform. The fruit flesh is white, and generally with a slightly red pigmentation under at ripening time and into the stone cavity. The fruit skin is very thick, with a luminous purple red blush on a red background. The stone is semi-clingstone and the size is small. Fruit taste is semi-sweet, very aromatic and with a high level of sugars.

Compared to 'CAKEREVE' white flat nectarine variety (U.S. Plant Pat. No. 26,769), the new variety named 'CAKESTAR' has generally a similar period of maturity, or ripens sometimes a few days later. The amount of flowers of the new variety 'CAKESTAR' is lower than the amount of flowers produced by the similar variety 'CAKEREVE'. Indeed, the new variety produces between 45 and 50 flowers per linear meter whereas the similar variety produces 50 to 60 flowers per linear meter. The pistillary basin of the new variety 'CAKESTAR' is generally very well closed whereas the pistillary basin of the 'CAKEREVE' variety is well closed.

Compared to the seed parent 'CAKEDELICE' white flat nectarine tree (not patented), the new variety named 'CAKESTAR' generally ripens 2 weeks earlier.

Compared to the pollen parent 'NECTARPERF' (U.S. Plant Pat. No. 23,357), the new variety named 'CAKESTAR' is a round and flattened nectarine whereas 'NECTARPERF' is a white round nectarine.

DETAILED DESCRIPTION

Referring more specifically to the pomological details of this new and distinct variety of white flat nectarine tree, the following was observed on trees in their third growing season (second year of production) under the ecological conditions prevailing at the orchards located near the town of Elne, Pyrénées-Orientales departement, France. All observations have been done on rootstock cultivars. Used rootstocks were 'INRA® GF677' (non-patented) trees. All major color code designations are by reference to The R.H.S. Colour Chart (Fourth Edition) provided by The Royal Horticultural Society of Great Britain.

TREE

Size:

*Generally*.—Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduced to 250 cm the next years.

Spread: Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

Vigor: Considered medium.

Productivity: Considered good to very good, and regular. Fruit set is spaced by thinning to develop the remaining fruit into the desired market sized fruit. The number of the fruit set varies with the prevailing climatic conditions and cultural practices employed during the bloom period, and is therefore not distinctive of the present variety. A reduced vegetation, obtained with pruning or green pruning, approximately 1 month or 1 month ½ before harvesting flat fruits, significantly promotes fruit qualities, especially growth, color and firmness. Moreover, contamination risks due to monilia or rot are significantly reduced. 'CAKESTAR' variety is not much sensitive to cracking of pistil cavity, to cork formation into peduncle cavity or to monilia.

Bearer: Very regular. The fruit distribution is considered homogenous on mixed branches and spurs having more than 1 year. Thinning of 2 fruits out of 3 was necessary for the tree valorisation. Thinning was necessary every year during the years of observation.

Form: The 'CAKESTAR' variety has naturally a semi-flared shape.

Density: Considered dense.

Hardiness: The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. Traditionally, flat fruits are more sensitive to critical low temperatures and to climatic variations, because of the flower morphology in which the ovule is less protected than in the classical round fruits. Thus, areas not much exposed to frost are recommended for trees growth. However 'CAKESTAR' trees seem to be very resistant to critical frosty weather.

TRUNK

Diameter: Approximately 39 millimeters in diameter when measured at a distance of approximately 20 centimeters above the soil level.

Bark texture: Considered rough, with lenticels.

Lenticels: Numerous lenticels are present. The number of lenticels reaches 5 lenticels per $cm^2$. The lenticels range in size approximately 2.5 to 4.0 millimeters in width, and about 1.0 to 1.3 millimeters in height.

Lenticel color: The lenticels show a beige to light orange color (RHS Greyed Orange 164 C or RHS Greyed Orange 164 D).

Bark coloration: At the base of the trunk the bark has a silver-grey color (RHS Grey 201 A or RHS Grey 201 B) darker than the lenticels color. This color evolves towards a brown color (RHS Brown 200 B or RHS Brown 200 C).

BRANCHES

Size: The branches are pruned to approximately 1.0 meter in length.

Diameter: Average as compared to other nectarine varieties. The current season shoots have a diameter of approximately 3.5 to 5.0 millimeters, and mature branches have a diameter of approximately 7.0 to 9.0 millimeters.

Surface texture: Smooth for current season shoots and rough, with lenticels. For mature branches, texture is rough and wood which is several years old has no furrowed appearance.

Crotch angles: Primary branches are considered variable, but the crotch angles are generally of 70 degrees from the horizontal axis. This particular characteristic is not considered distinctive of the variety, however.

Current season shoots:

Internode length: Generally between 22.0 to 29.0 millimeters.

*Color*.—The color of new shoot tips is considered green (RHS Yellow Green 144 A or RHS Yellow Green 144 B) on lower part of new shoot tips, whereas the upper part is darker and colored in brown-purple (RHS Greyed Purple 187 B), depending on the level on the tip and the sunlight exposure.

Mature branches:

Internode length: Generally between 14.0 and 19.0 millimeters.

Color of mature branches: Brown (RHS Grey Brown 199 A or RHS Grey Brown N 199 A or RHS Grey Brown N 199 B).

Lenticels: Numerous lenticels are present on mature branches. The number of lenticels reaches 2 lenticels per $cm^2$. The size of lenticels is considered small. The lenticels range in size from approximately 2.2 to 3.0 millimeters in width, and about 1.0 to 1.2 millimeters in height. The lenticel shape is round and slightly stretched.

Lenticel color: The lenticels on mature branches have a light beige color (RHS Greyed Yellow 161 C or RHS Greyed Yellow 161 D).

LEAVES

Size: Considered medium for the species. The ratio leaf length/leaf width is 4.33.

Leaf length: Approximately 147.0 to 168.0 millimeters with leaf petiole. The medium length is about 158.6 millimeters.

Leaf width: Approximately 33.0 to 42.0 millimeters. The medium width is 36.6 millimeters.

Leaf base shape: Concave.

Leaf form: Lanceolate.

Leaf tip form: Short, pointed and acuminate.

Leaf color:

*Upper leaf surface*.—Dark Green (RHS Green Group 137 A).

*Lower surface*.—A lighter green (RHS Green 137 C) than the upper leaf surface color.

Leaf texture: Smooth and glabrous.

Leaf venation: Pinnately veined.

Mid-vein:

*Color*.—Light green, almost cream white (RHS Yellow Green 145C). The color may evolve with maturity.

Leaf margins: Slightly undulating.

Form: Considered slightly dentate.

Uniformity: Leaves are isolated or grouped by 2 or 3. In this last case, one leaf of normal size is found with one or two smaller leaves (at least 50% smaller).

Leaf petioles:

*Size*.—Considered medium.

*Length*.—About 9.0 to about 12.0 millimeters. The medium length is about 10.4 millimeters.

*Diameter*.—About 1.5 to about 2.1 millimeters. The medium diameter is about 1.78 millimeters.

Petioles color:

*Upper petiole surface*.—Green (RHS Green Group 143 C).

*Lower surface*.—Light green (RHS Yellow Green 145 B to RHS Yellow Green 145 C).

Leaf glands:

*Size*.—Considered medium to large. Their length is about 1.5 to 1.8 millimeters and their width is about 1.0 millimeter.

*Number*.—Generally 2 glands per leaf.

*Type*.—Reniform.

*Margins*.—Smooth and regular.

*Color*.—On young leaves, leaf gland color is considered a light green (RHS Green 145 B). On older leaves, leaf gland color turns to a dark brown (RHS Grey Brown 199 A to RHS Grey Brown 199 B).

Leaf stipules:

*Generally*.—No leaf stipules were observed. But as seen in the characteristic relative to the leaves uniformity, it is possible to find leaves by groups of 2 or 3, with a normal-size leaf and smaller ones.

FLOWERS

Flower buds:

*Generally*.—At pre-floral stage of development, the floral buds are conic in form with a round tip. Their form is evolving until blooming, with variable dimensions. Just before blooming, floral buds are approximately 8.0 to 10.0 millimeters wide and approximately 15.0 to 19.0 millimeters long.

*Color*.—This characteristic is dependent upon the proximity to bloom. At pre-floral stage of development, the bottom of the flowers buds, formed by the sepals, is of purple-brown color (RHS Greyed Purple 183 A) and yellow green at the base (RHS Yellow Green 146 B). The corolla, formed by the petals, is generally of medium pink color (RHS Red Purple 65 B) on both faces. Petal color shows an evolution until the end of flowering.

Hardiness: The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: The blooming time generally begins at the end of February or early in March. The first bloom was observed on Mar. 9, 2015.

Blooming time: Considered medium in relative comparison to other commercial nectarine cultivars grown in the Pyrénées-Orientales departement, France. The date of full bloom is observed generally at the middle of the blooming period. Thus the full bloom was observed in 2015, from March 9$^{th}$ until March 18$^{th}$, then from February 21$^{st}$ until Mar. 4, 2016 and them from February 28$^{th}$ until Mar. 10, 2017.

Duration of bloom: Medium, approximately between 10 to 13 days. This characteristic varies slightly with the prevailing climatic conditions and cultural practices.

Flower type: The variety is considered to have a showy type flower.

Flower size: Considered medium to large. Flower diameter at full bloom is approximately 32.0 to 36.0 millimeters.

Bloom quantity: Considered abundant, approximately between 40 and 50 flowers per meter, with a high rate of fruit set. The bloom is heterogeneous, and the bloom quantity is more important on the top of the tree.

Flower bud frequency: Generally 2 flower buds appear per node, occasionally 1.

Petal size:

*Generally*.—Considered medium to large.

Length: Generally between 18.0 and 20.0 millimeters. The medium length is 19.0 millimeters.

Width: Generally between 15.0 and 17.0 millimeters. The medium width is about 16.0 millimeters.

Petal form: Round-shaped.

Petal count: Generally 5.

Petal texture: Smooth and soft.

Petal color: At the stage F of blooming, when the flower is fully opened, both surfaces of the petal are colored with a pink (RHS Red 62 B) or medium pink color (RHS Red Purple 65 B or RHS Red Purple 65C or RHS Red Purple 65 D) on both faces when young, becoming slightly darker until the end of blooming.

Fragrance: Moderate.

Petal claw:

*Form*.—The claw is considered to have a narrow form.

*Color*.—Dark pink (RHS Red Purple 61 B), darker than the petal color.

*Length*.—Approximately 1.5 to 2.0 millimeters.

*Width*.—Approximately 1.0 millimeter.

Petal margins: Generally considered smooth to moderately wavy, sinuate at their base.

Petal apex:

*Generally*.—The petal apices are wide dome shaped.

Flower pedicel:

*Length*.—Considered medium and having an average length of approximately 2.5 to 3.0 millimeters.

*Diameter*.—Considered average, approximately 1.5 to 2.0 millimeters.

*Color*.—Green (RHS Yellow Green 145 A).

Calyx:

*Internal surface texture*.—Smooth and glabrous.

*Color*.—At the stage F of blooming, when the flower is opened, the inner surface of the calyx namely the flower receptacle is considered greenish yellow (RHS Yellow Green 153 C). The outer surface of the calyx is considered of purple-brown color (RHS Greyed Purple 183 A or RHS Greyed Purple 187 B).

Sepals:

*Sepal count*.—5.

*Surface texture*.—The outer surface has a fine pubescent texture.

*Margins*.—Smooth.

*Size*.—Medium.

*Form*.—Conic with a round tip.

*Length*.—Approximately 5.0 to 6.0 millimeters.

*Width*.—Approximately 4.0 to 5.0 millimeters.

*Color*.—At pre-floral stage of development (stage A) the sepals are colored in purple-brown color (RHS Greyed Purple 183 A) and green at their base (RHS Yellow green 146 B). At the stage F of blooming, the inner surface of the sepals is considered greenish yellow to brown (RHS Yellow Green 153 C or RHS Yellow Green 145 A). The outer surface of the sepals is considered of purple-brown color (RHS Greyed Purple 183 A or RHS Greyed Purple 187 A).

Average number of stamens per flower: Approximately 36 to 46 stamens per flower.

Anthers:

*Color*.—At an early stage of maturity, anthers are colored with an orange yellow color (RHS Yellow Orange 16 A to RHS Yellow Orange 16 B) . The color may evolve with maturity to turn in a red or red orange color (RHS Red Group N34 A or RHS Greyed Red Group 178 A or RHS Red 46 A or RHS Red 46 B).

*Size*.—Small to medium.

*Shape*.—Reniform.

Pollen production: Pollen is abundant, and has a yellow (RHS Yellow 11A) or an orange yellow color (Approximately RHS Yellow Orange 17 B to RHS Yellow Orange 17 C) which may evolve with maturity. The present variety is considered auto-fertile (self-pollinating).

Filaments:

*Size*.—Medium length, between 10.0 and 17.0 millimeters in length. Filament length is generally higher than the pistil's length.

Color: Considered white (RHS White 155 D) or pale pink (RHS Red Purple 62 C to Red Purple 62 D) at the beginning of flowering to a pink (RHS Red 56 A) or a darker pink (RHS Red Purple 73 A to RHS Red Purple 73 B) at the end of flowering. The color becomes darker during the blooming.

Pistil:

*Number*.—Usually 1.

*Generally*.—Average in size.

*Length*.—Approximately 14.0 to 17.0 millimeters including the ovary. Pistil's length is generally smaller than the filament's length, or equal to the filament's length.

*Color*.—Considered a very pale green (RHS Yellow Green 145 C or RHS Yellow Green Group 151 D) at the beginning of the blooming. The color evolves during the blooming, becoming more light (RHS Yellow Green 150 D) and sometimes very slightly pink (RHS Red Group 36D) at the end of the blooming.

Ovary:

*Pubescence*.—Absent.

*Height*.—Between 1.5 and 2.0 millimeters.

*Diameter*.—Between 1.5 and 2.0 millimeters.

*Color*.—Green (RHS Yellow Green 145 A or RHS Yellow Green 145 B).

Stamen:

*Size compared to petals*.—The size of stamen is smaller than the size of petals.

Stigma:

*Position compared to anthers*.—The stigma is below the anthers.

*Diameter*.—Approximately 1.0 millimeter.

*Color*.—Pale green to slightly yellow (RHS Yellow Green 154 B)

FRUIT

Maturity when described: Firm in ripe conditions (shipping ripe).

Date of first picking: Jul. 4, 2014.

Date of last picking: The date of harvest varies slightly with the prevailing climatic conditions. The 'CAKESTAR' variety has a medium date of picking, and a grouped maturity. The maturity is grouped within 8 to 9 days and the harvest is generally performed in two runs. Last known picking times carry on July $4^{th}$ until Jul. 12, 2014 then on July $15^{th}$ until Jul. 22, 2015,then on July $18^{th}$ until Jul. 25, 2016 and then on July $10^{th}$ until Jul. 16, 2017.

Size:

*Generally*.—Homogeneous in size. Considered medium to large.

Average cheek diameter: Approximately 68.0 to 75.0 millimeters.

Average axial diameter: Approximately 43.0 to 45.0 millimeters.

Typical weight: Generally about 115.0 to 165.0 grams. The average weight is 137.6 grams. This characteristic is highly dependent upon the prevailing cultural practices, and therefore is not particularly distinctive of the variety.

Fruit form:

*Generally*.—Round and flattened. The fruit is generally uniform in symmetry, viewed from the suture's plane.

Suture:

Fruit suture: Wide-mouthed and slightly marked, extending from the base to the apex. No apparent callousing or stitching exists along the suture line. Not pointed.

*Color*.—The suture has generally a similar color to the whole fruit color, a luminous purple red (RHS Greyed Purple 187 A).

Ventral surface:

*Form*.—Smooth.

Apex: Slightly depressed.

Base: Semi-flared, shallow.

Stem cavity: Average depth of the stem cavity is about 6.0 to 8.0 millimeters. Average width is about 14.0 to 17.0 millimeters.

Fruit skin:

*Thickness*.—Considered thick and strong, and the adherence of skin to flesh is strong to medium, depending on the fruit maturity.

*Texture*.—Very smooth, without any fuzz.

*Taste*.—Semi-sweet, sugary.

*Tendency to crack*.—None observed.

Color:

*Blush color*.—This blush color is a luminous purple red (RHS Greyed Purple 187 A). The purple red blush covers the entirety of the fruit skin surface.

Fruit stem: Medium in length, approximately 7.0 millimeters.

Diameter: Approximately 3.5 millimeters.

Color: Pale green (RHS Yellow Green 145 A to RHS Yellow Green 145 B).

Flesh:

*Ripens*.—Very homogenously, slowly. The flesh has a long shelf life.

*Texture*.—Very firm, very dense, crunchy, melting, juicy at harvest maturity stage.

*Fibers*.—Not fibrous.

*Aroma*.—Very pronounced.

*Eating quality*.—Considered very good, aromatic.

*Flavor*.—Considered semi-sweet. The Brix is generally superior to 13 and acidity comprised between 6 and 9 meq/100 ml.

*Juice*.—Juicy to very juicy at complete maturity.

*Brix*.—Generally 15.0 to 16.0 degrees. This characteristic varies slightly with the number of fruit per tree; prevailing cultural practices; and the surrounding climatic conditions.

*Flesh color*.—White flesh, slightly greenish (RHS Green White 157 B), usually with a slightly red pigmentation into the stone cavity (RHS Red Purple 60 B) and a slightly red pigmentation under the skin of the fruit (RHS Red 51 B) at ripening time.

STONE

Type: Semi-Clingstone, more or less semi-adherent depending on the fruit maturity.

Size: Considered small for the variety. The stone size varies significantly depending upon the tree vigor, crop load and prevailing growing conditions.

Length: Approximately 15.0 to 16 millimeters.
Width: Approximately 22.0 to 24.0 millimeters.
Diameter: Approximately 20.0 to 22.0 millimeters.
Form: Flattened.
Base: Straight.
Apex:
*Shape*.—The stone apex is flattened.
Stone cavity: Considered small size, with flattened form and dimensions corresponding to the stone's dimensions.
Stone surface:
*Surface texture*.—The pit is transversely furrowed on its entire surface. Furrows are deeper and more oblate on lateral sides.
*Ridges*.—The surface texture is generally characterized by more prominent ridges along the ventral edges and at the apical tip.
Ventral edge:
*Width*.—Approximately 3.0 to 4.0 millimeters at mid-suture.
Dorsal edge:
*Shape*.—Grooved.
Stone color: The color of the dry stone is generally considered light orange brown (RHS Greyed Orange 165 B or RHS Greyed Orange 165 C).
Tendency to split: Splitting is very low or absent, depending on climatic conditions between blooming period and stone hardening.
Kernel:
*Size*.—The kernel is considered small.
*Length*.—Approximately 4.0 millimeters.
*Width*.—Approximately 7.0 millimeters.
*Thickness*.—Approximately 6.0 millimeters.
*Form*.—Considered flattened and elliptic. Sometimes double.
*Pellicle*.—The pellicle of the kernel has a short pubescence.
*Color*.—The kernel skin is orange-brown colored (RHS Greyed Orange N167 A to RHS Greyed Orange N167 B). The almond, which is the seed of the kernel, is white (RHS White 155 D) and has a bitter taste. The kernel and its embryo are mature at the time of fruit maturity.
Use: The subject variety 'CAKESTAR' is considered to be a white flat nectarine tree of the medium season of maturity, and which produces fruits that are considered firm, attractively colored with a very luminous purple red on the whole fruit skin. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.
Keeping quality: Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.
Shipping quality: Considered very good. The fruit of the new white flat nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.
Resistance to insects and disease: No particular susceptibilities were noted. The present variety is not very sensitive to Monilia or rot. The pistil cavity is completely closed, generally without any cork formation. Although the new variety of white flat nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of white flat nectarine tree as illustrated and described, characterized by fruits with high eating quality and very long shelf life without alteration before and after harvesting, with a very well closed pistillary basin, with a semi-sweet white flesh, with a slightly red pigmentation under the fruit skin at ripening time and into the stone cavity, and an attractive luminous skin colored with a purple red blush on the whole skin surface.

* * * * *